United States Patent
Tsubota et al.

(10) Patent No.: US 9,828,611 B2
(45) Date of Patent: Nov. 28, 2017

(54) EXOGENOUS GENE EXPRESSION VECTOR, TRANSFORMANT DISCRIMINATION MARKER, AND TRANSFORMANT

(71) Applicant: NATIONAL INSTITUTE OF AGROBIOLOGICAL SCIENCES, Tsukuba-shi, Ibaraki (JP)

(72) Inventors: Takuya Tsubota, Tsukuba (JP); Keiro Uchino, Tsukuba (JP); Hideki Sezutsu, Tsukuba (JP); Hiromitsu Tanaka, Tsukuba (JP)

(73) Assignee: NATIONAL INSTITUTE OF AGROBIOLOGICAL SCIENCES, Tsukuba-Shi, Ibaraki (JP)

( * ) Notice: Subject to any disclaimer, the term of this patent is extended or adjusted under 35 U.S.C. 154(b) by 0 days.

(21) Appl. No.: 14/911,639

(22) PCT Filed: Aug. 6, 2014

(86) PCT No.: PCT/JP2014/071353
§ 371 (c)(1),
(2) Date: Feb. 11, 2016

(87) PCT Pub. No.: WO2015/022971
PCT Pub. Date: Feb. 19, 2015

(65) Prior Publication Data
US 2016/0194661 A1    Jul. 7, 2016

(30) Foreign Application Priority Data
Aug. 14, 2013 (JP) ................... 2013-168655

(51) Int. Cl.
*C12N 15/09* (2006.01)
*C12N 15/00* (2006.01)
*A01K 67/033* (2006.01)
*C12N 15/85* (2006.01)
*C12Q 1/68* (2006.01)
*A01K 67/04* (2006.01)

(52) U.S. Cl.
CPC ...... *C12N 15/8509* (2013.01); *A01K 67/0339* (2013.01); *A01K 67/04* (2013.01); *C12Q 1/6897* (2013.01); *A01K 2217/052* (2013.01); *A01K 2227/706* (2013.01); *A01K 2267/0393* (2013.01); *C12N 2015/859* (2013.01)

(58) Field of Classification Search
None
See application file for complete search history.

(56) References Cited

PUBLICATIONS

Tamura et al., "Germline transformation of the silkworm Bombyx mori L. using a piggyBac transposon-derived vector", Nature America Inc., 2000, vol. 18, pp. 81-84.
Imamura et al., "Targeted Gene Expression Using the GAL4/UAS System in the Silkworm Bombyx mori", Genetics Society of America, 2003, vol. 165, pp. 1329-1340.
Thomas et al., "3XP3-EGFP marker facilitates screening for transgenic silkworm Bombyx mori L. from the embryonic stage onwards", Insect Biochemistry and Molecular Biology, 2002, vol. 32, pp. 247-253.
Masumoto et al., "A Baculovirus Immediate-Early Gene, ie1, Promoter Drives Efficient Expression of a Transgene in Both Drosophila melanogaster and Bombyx mori", PLOS One, vol. 7, No. 11, pp. 1-10.
Sosalegowda et al., "Molecular characterization of heat shock proteins 90 (HSP83?) and 70 in tropical strains of Bombyx mori", Proteomics, 2010, vol. 10, pp. 2734-2745.
Tsubota et al., "Identification of a Novel Strong and Ubiquitous Promoter/ Enhancer in the Silkworm Bombyx mori", G3: Genes | Genomes| Genetics, 2014, vol. 4, pp. 1347-1357.
Shimomura et al., "KAIKObase: An integrated silkworm genome database and data mining tool", BMC Genomics, 2009, vol. 10, No. 486, pp. 1-8.
International Search Report dated Nov. 18, 2014 for International Application No. PCT/JP2014/071353. (2 pages).

*Primary Examiner* — Maria Leavitt
*Assistant Examiner* — Kimberly A Aron
(74) *Attorney, Agent, or Firm* — Lucas & Mercanti, LLP

(57) ABSTRACT

This invention is intended to develop a promoter that can strongly induce marker gene expression throughout an embryo, so as to simply, efficiently, and accurately identify a transgenic insect at an early developmental stage, and to provide a gene expression vector into which such promoter has been incorporated as a transformant discrimination marker. Such exogenous gene expression vector comprises a polynucleotide comprising the nucleotide sequence as shown in SEQ ID NO: 1 as a promoter.

9 Claims, 8 Drawing Sheets

White light

Adult

Pupa

Larva

Embryo

Fluorescence

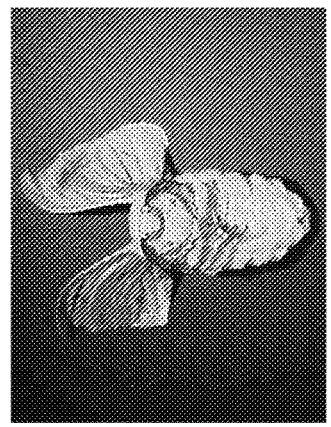
FIG. 4A
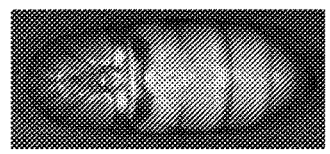
FIG. 4B'
FIG. 4C'
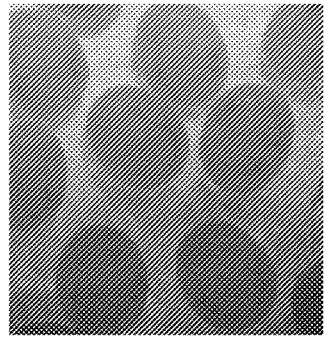
FIG. 4D'
White light
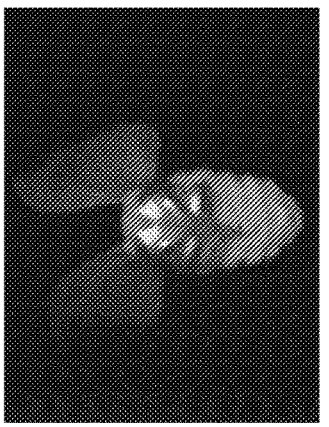
FIG. 4A'
FIG. 4B'
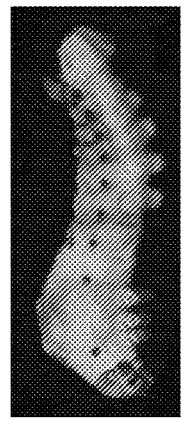
FIG. 4C'
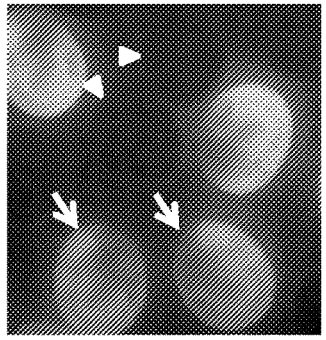
FIG. 4D'
GFP
Embryo    Larva    Pupa

EXOGENOUS GENE EXPRESSION VECTOR, TRANSFORMANT DISCRIMINATION MARKER, AND TRANSFORMANT

CROSS-REFERENCE TO RELATED APPLICATIONS

This application is a 371 of PCT/JP2014/071353, filed Aug. 6, 2014, which claims the benefit of Japanese Patent Application No. 2013-168655, filed Aug. 14, 2013.

TECHNICAL FIELD

The present invention relates to an exogenous gene expression vector comprising a promoter that can strongly induce expression of an objective gene, a transformant discrimination marker using such expression vector, and a transformant into which such expression vector and discrimination marker have been introduced.

BACKGROUND ART

Genetic engineering techniques are essential for analysis of gene functions and production of useful proteins. In the past, production of useful proteins had usually used *E. coli* or yeast as hosts; however, such hosts had serious problems in terms of difficulty in mass-production. In recent years, accordingly, the silkworm (*Bombyx mori*) that enables synthesis of large quantities of proteins within a short period of time is hitting the limelight as a protein mass-production system. When silkworm is used as a host, a technique for producing a transformant into which a foreign gene has been introduced in its cell; that is, transgenic silkworm, becomes critical. A technique of stably maintaining a foreign gene in the genome of *Bombyx mori* with the use of the piggyBac transposon has been established (Tamura, T. et al., 2000, Nat. Biotechnol., 18: 81-84).

In addition to a technique of preparing a transformant, genetic engineering techniques require a technique of accurately and simply discriminating a transformant that carries an introduced foreign gene from a host that does not carry such foreign gene (i.e., a non-transformant). When hosts are insects, objective genes are introduced into the host cells with marker genes such as fluorescent proteins and promoter that controls the expression thereof at the time of transformation, and whether or not the host cells have been transformed is determined based on the expression of marker genes. When implementing such technique, accordingly, it is critical to select a promoter that can strongly and extensively induce the expression of marker genes.

In the case of silkworm, a systemic actin A3 gene promoter (Non-patent Literatures 1 and 2), the eye-specific 3×P3 promoter known to be versatile among various organism species (Non-patent Literature 3), and the immediate-early IE1 promoter (Non-patent Literature 4) have been primarily used as the promoters described above. However, these promoters had problems described below.

First of all, activity of the A3 promoter is weak at the embryonic stage, and a transformant cannot be discriminated at an early developmental stage, as shown in FIG. 1B. Accordingly, all the individuals that had been subjected to transformation had to be uniformly grown up to the larval stage at which expression of marker genes became identifiable. Therefore, the significant amounts of useless efforts and labors were necessitated and wasted expense accrued. In addition, larvae move around. Accordingly, when a phonotype based on a marker gene cannot be visually distinguished under visible light, unlike a body color, it was difficult to select individuals of interest. When a marker gene encodes a fluorescent protein, for example, a fluorescence-emitting individual needs to be selected while continuously applying an excitation light to silkworm larvae that move around.

Subsequently, the 3×P3 promoter already exhibits activity at the embryonic stage, and the problem of the A3 promoter thus does not arise. As shown in FIG. 1D, however, the site of expression is limited to a very small portion of an embryo (a portion indicated with an arrow in the figure). Accordingly, the technical skills to identify and determine the individuals of interest were required. When an expression vector carrying such promoter is inserted into a host genome, expression of the objective gene may be inhibited depending on the effect of an insertion site. In such a case, discrimination of the transformants became difficult for even a person skilled in the art. In addition, the duration during which the objective gene expression could be confirmed at the early developmental stage was as short as 1 or 2 days, disadvantageously.

In the case of IE1 promoter, activity of expression induction was not observed in the fat body, spermary, or ovary. This indicates that activity of gene expression induction was not effective throughout the body.

CITATION LIST

Non-Patent Literature

Non-patent Literature 1: Tamura, T. et al., 2000, Nat. Biotechnol., 18: 81-84

Non-patent Literature 2: Imamura, M., et al, 2003, *Bombyx mori*, Genetics 165: 1329-1340

Non-patent Literature 3: Thomas, J.-L. et al., 2002, Insect Biochem. Mol. Biol., 32: 247-253

Non-patent Literature 4: Masumoto et al., 2012, PLoS One, e49323

SUMMARY OF THE INVENTION

It is an object of the present invention to develop a promoter that can strongly induce expression of marker genes in a whole embryo, so as to distinguish transgenic insects in a simple, efficient, and accurate manner at an early developmental stage. It is another object of the present invention to provide a transformant discrimination marker, which is a gene expression vector into which the promoter described above has been introduced.

A further object of the present invention is to provide a gene expression vector that can strongly express a gene encoding a protein of interest throughout all the developmental stages from the early developmental stage with the use of activity of the promoter described above.

In order to solve the above objects, the present inventors prepared numerous enhancer trap lines of silkworms comprising transposons randomly inserted into the genomes. They succeeded in separating a line (the AyFib-431a line) that can strongly express reporter genes in the whole body from an early developmental stage, which is a desirable property in order to solve the objects of the present invention. As a result of analysis of the insertion site of transposon into the genome of this line, a transposon was found to be inserted into 5'-UTR of the hsp90 gene, and the hsp90 gene promoter was found to have induced the expression of a reporter gene in the transposon.

The present invention has been completed on the basis of the finding described above, and the present invention provides the following.

(1) An exogenous gene expression vector comprising a polynucleotide comprising the nucleotide sequence shown in SEQ ID NO: 1 as a promoter.
(2) The exogenous gene expression vector according to (1) comprising a polynucleotide comprising the nucleotide sequence shown in SEQ ID NO: 2 as a promoter.
(3) The exogenous gene expression vector according to (1) or (2) used for transformation of a species belonging to the order Lepidoptera.
(4) A transformant discrimination marker of a species belonging to the order Lepidoptera consisting of a gene expression vector comprising a promoter comprising a polynucleotide comprising the nucleotide sequence shown in SEQ ID NO: 1 and a marker gene or a functional nucleotide fragment thereof on the downstream of the promoter.
(5) The transformant discrimination marker according to (4), which is consisting of a gene expression vector comprising a promoter comprising a polynucleotide comprising the nucleotide sequence shown in SEQ ID NO: 2 and a marker gene under the control of such promoter.
(6) A transformant comprising the exogenous gene expression vector according to any of (1) to (3) or the transformant discrimination marker according to (4) or (5).
(7) The transformant according to (6), which comprises the exogenous gene expression vector or the transformant discrimination marker in the genome.

This description includes part or all of the content as disclosed in the description and/or drawings of Japanese Patent Application No. 2013-168655, which is a priority document of the present application.

BRIEF DESCRIPTION OF THE DRAWINGS

FIG. 4 shows GFP expression in the transgenic silkworm into which the exogenous gene expression vector shown in FIG. 3 has been introduced. A and A' indicate embryos, B and B' indicate larvae, C and C' indicate pupae, and D and D' indicate adults. A, B, C, and D are an image obtained under white light, and A', B', C' and D' are GFP fluorescent images. As in the case of the original AyFib-431a line shown in FIG. 2, strong GFP expression was observed throughout all the developmental stages from the embryo to the adult. In A', an arrow indicates an embryo into which the exogenous gene expression vector has been introduced, and an arrow head indicates an embryo into which such expression vector has not been introduced.

EMBODIMENTS FOR IMPLEMENTING THE INVENTION

Figure 1A:
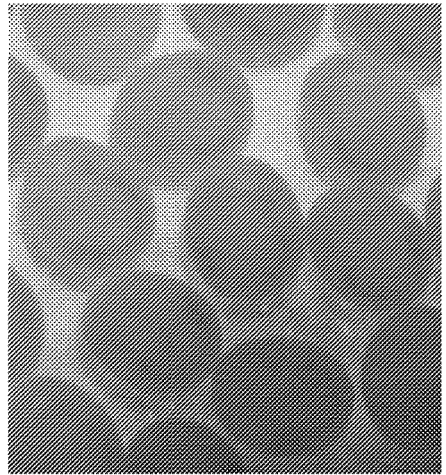
FIG. 1 shows an embryo of a transgenic silkworm having a transformant discrimination marker comprising a marker gene ligated to the downstream of a conventional promoter. A and B show a transgenic silkworm comprising a systemic actin A3 gene promoter and the GFP gene ligated to the downstream of the gene promoter. C and D show a transgenic silkworm comprising the eye-specific 3×P3 promoter and the DsRed gene ligated to the downstream of the promoter. A and C show an image obtained under white light, and B and D show a fluorescent image obtained in the same field as A and C. An arrow in D indicates a site at which DsRed expression is observed. A conventional promoter is not sufficient to identify a transformant based on marker gene expression at the early developmental embryo stage.
Figure 1B:
Figure 1C:
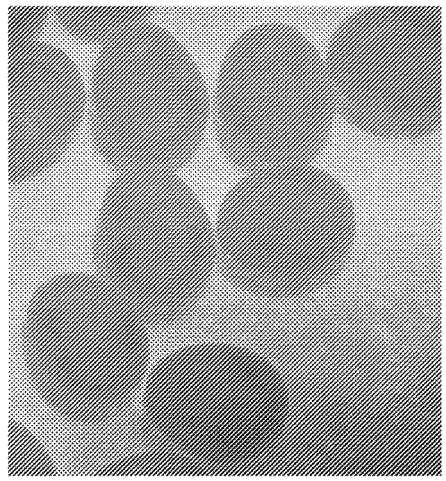
Figure 1D:
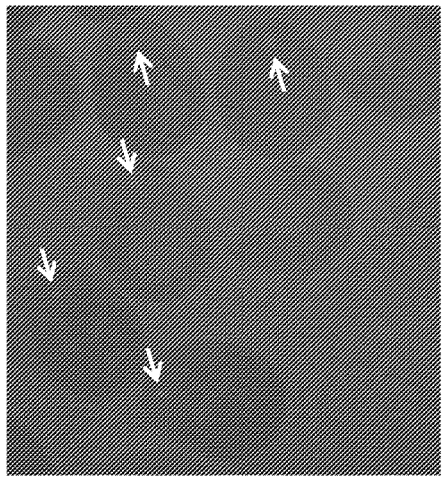
Figure 2D:
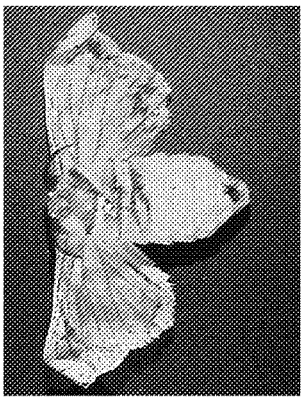
FIG. 2 shows DsRed expression in the AyFib-431a line selected from among the silkworm enhancer trap lines. A and A' indicate embryos, B and B' indicate larvae, C and C' indicate pupae, and D and D' indicate adults. A, B, C, and D are an image obtained under white light, and A', B', C' and D' are fluorescent images. Strong DsRed expression is observed throughout all the developmental stages from the embryo to the adult. In A', an arrow indicates an embryo into which a transposon used for an enhancer trap has been introduced (i.e., the AyFib431a line), and an arrow head indicates an embryo into which such transposon has not been introduced.
Figure 2C:
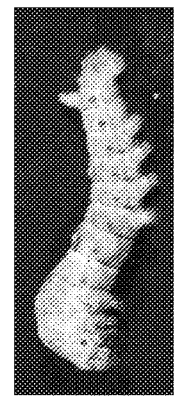
Figure 2B:
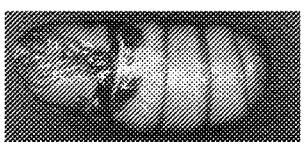
Figure 2A:
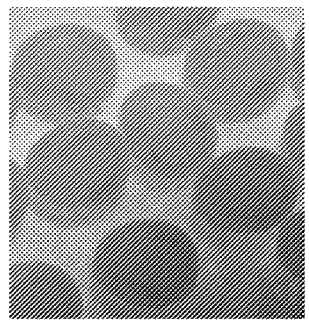
Figure 2D:
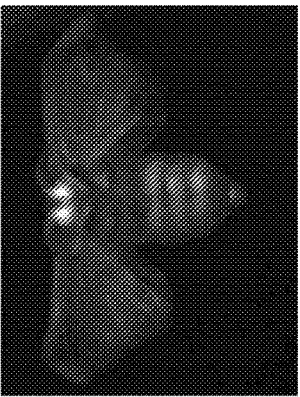
Figure 2C:
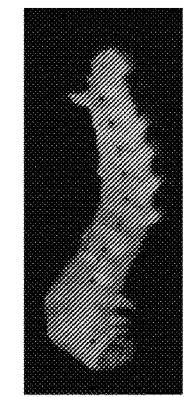
Figure 2B:
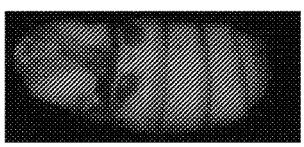
Figure 2A:
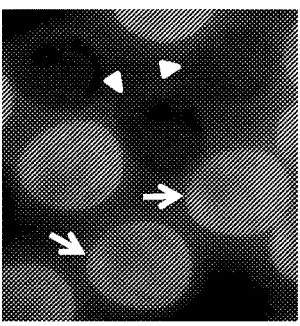

1. Exogenous Gene Expression Vector
1-1 Summary

The first aspect of the present invention concerns an exogenous gene expression vector. The exogenous gene expression vector according to this aspect comprises a nucleotide sequence based on a promoter derived from silkworm obtained with the use of an enhancer trap. An objective gene may be incorporated into the downstream of such nucleotide sequence, and the resulting expression vector may be introduced into an insect cell. Thus, the objective gene can be expressed throughout all the stages from the embryo to the adult throughout the body.

1-2. Constitution

The term "gene expression vector" used herein refers to a unit of an expression system comprising expressibly an objective gene or a nucleotide fragment thereof (hereafter, such objective gene or nucleotide fragment thereof is often referred to as an "objective gene or the like") and capable of inducing expression of an objective gene or the like.

Also, the term "exogenous gene expression vector" used herein refers to an exogenous gene expression vector, which has been introduced from the outside via artificial manipulation. An endogenous gene expression vector derived from an exogenous gene expression vector, such as a progeny of transgenic insects, is within the scope of the exogenous gene expression vector according to the present invention.

When an objective gene or the like is incorporated in "expressibly" herein, an objective gene or the like can be or has been incorporated into the gene expression vector according to this aspect, so that an objective gene or the like can be expressed therein. Specifically, an objective gene or the like can be or has been positioned under the control of a promoter within the exogenous gene expression vector.

The exogenous gene expression vector according to this aspect comprises, as an essential constitutional element, a promoter that controls expression of an objective gene or the like. Such expression vector can also comprise, as selective constitutive elements, an objective gene or the like, an enhancer, a multi-cloning site, 5' UTR, 3' UTR, signal peptide DNA, a terminator, marker gene(s), an insulator, inverted terminal repeat sequences of a transposon, or the like. Hereafter, constitutional elements of the gene expression vector according to the present aspect are described in detail.

(1) Promoter

A promoter is an essential constitutional element that plays a key role of the exogenous gene expression vector of this aspect.

The promoter comprised in the exogenous gene expression vector of this aspect comprises, as the minimal active unit, a polynucleotide comprising the nucleotide sequence consisting of 1649 bases shown in SEQ ID NO: 1. This nucleotide sequence is based on the sequence of a promoter that controls expression of the hsp90 gene of *Bombyx mori* (i.e., the hsp90 gene promoter). A length of the promoter is not particularly limited, as long as it is 1649 bases or longer as described above. Preferably, a polynucleotide comprising the nucleotide sequence shown in SEQ ID NO: 1 is extended by a length up to 2 kb, 1.5 kb, 1.3 kb, 1.2 kb, 1.0 kb, 500 bp, 400 bp, 300 bp, 250 bp, or 200 bp from the 5' terminus. A nucleotide sequence of a promoter to be extended is not particularly limited, except for the 1649 nucleotides described above. It is preferable that a nucleotide sequence be located adjacent to the upstream region of the nucleotide sequence shown in SEQ ID NO: 1 (i.e., on the 5' terminal side) in the nucleotide sequence of the hsp90 gene promoter of silkworm. It is particularly preferable that a promoter comprise a polynucleotide comprising the nucleotide sequence consisting of 1884 bases shown in SEQ ID NO: 2.

In the exogenous gene expression vector according to this aspect, a promoter is constructed, so that an objective gene or the like described below can be located within the control region of a downstream region (on the 3' terminal side).

In the exogenous gene expression vector according to this aspect, the promoter is, as described in the examples below, a constitutively active promoter that can continuously and ubiquitously control expression of an objective genet or a fragment thereof in an introduced-insect cell from the embryonic developmental early stage to the adult stage.

(2) Objective Gene or the Like

The term "an objective gene or the like (or an objective gene or a nucleotide fragment thereof)" used herein refers to a gene encoding a protein of interest or a peptide fragment thereof, or a nucleotide fragment thereof. Alternatively, the term refers to a polynucleotide encoding a functional nucleic acid.

The term "a protein of interest or a peptide fragment thereof" used herein refers to a protein of interest or a peptide fragment thereof to be expressed in an insect host cell into which the exogenous gene expression vector of the present aspect is to be introduced. Such protein may be a structural or functional protein. Examples of structural proteins include fibrous proteins, such as collagen, actin, myosin and fibroin, keratin, and histone. Examples of functional proteins include peptide hormones, such as insulin, calcitonin, parathormone and growth hormones, cytokines, such as epidermal growth factors (EGF), fibroblast growth factors (FGF), interleukin (IL), interferon (IFN), tumor necrosis factor α (TNF-α) and transforming growth factor β (TGF-β), transcription factors including GAL4, immunoglobulin, serum albumin, hemoglobin, and enzymes. The protein of interest may be a wild-type or mutant protein. For example, a mutant protein resulting from a gain-of-function mutation may be used. In addition, the protein or a peptide fragment thereof may be active or inactive because an inactive mutant protein is capable of imparting dominant negative effects to insects into which the gene expression vector of the present aspect has been introduced. In general, however, an active protein or an active peptide fragment thereof is preferable. The protein may be a chimeric protein composed of whole or a part of a plurality of different proteins fused to each other. An example is a chimeric protein composed of a signal peptide of a sericin protein that is expressed specifically in the middle silk gland of silkworm and a fibroin H-chain (Fib H) protein that is expressed specifically in the posterior silk gland. In addition, the protein may be derived from an organism species that is different from a host organism species into which the exogenous gene expression vector of the present aspect is to be introduced. For example, a protein encoded by the exogenous gene expression vector of the present aspect may be human-derived collagen, and a host into which the exogenous gene expression vector is to be introduced may be silkworm.

The term "functional nucleic acid" used herein refers to a nucleic acid molecule having particular biological functions, such as enzymatic functions, catalytic functions, or biological inhibitory or enhancing functions (e.g., inhibition or enhancement of transcription or translation) in an organism or in a cell. Specific examples include an RNA interference agent, a nucleic acid aptamer (e.g., an RNA aptamer), a ribozyme, an U1 adaptor, and a transcription factor-binding region. An RNA interference agent is a substance that can induce RNA interference (RNAi) in vivo and degrade a transcription product of the target gene, thereby suppressing expression of the gene (i.e., gene silencing). Examples thereof include shRNA (short hairpin RNA), miRNA (micro RNA, including pri-miRNA and pre-miRNA), and antisense RNA.

The exogenous gene expression vector of the present aspect may comprise a plurality of objective genes or the like. When objective genes or the like encode proteins, such objective genes or the like may encode the same protein or different proteins. In such a case, it is necessary that the objective genes or the like be located within the control region of the promoter. An objective gene or the like can encode monocistronic mRNA or polycistronic mRNA.

An objective gene or the like is an expressional object and is a constitutionally important element in the exogenous gene expression vector of the present aspect. However, an objective gene or the like is not a constitutionally essential element. This is because a region into which an objective gene or the like is to be incorporated is a "cassette region" that can be exchanged in the exogenous gene expression vector, according to need. Accordingly, such cassette region may be "empty" until an objective gene or the like is incorporated thereinto. When the cassette region is empty, however, there is no objective object to be expressed therein. Thus, it does not function as the exogenous gene expression vector of the present aspect. That is, the exogenous gene expression vector of the present aspect in which a cassette region into which an objective gene or the like is to be incorporated is empty can be understood as an exogenous gene expression vector in the rest state.

(3) Multi-Cloning Site

A multi-cloning site is a selective constitutive element of the exogenous gene expression vector of the present aspect. The type and the number of constitutive nucleotide sequences and the restriction enzyme sites therein are not particularly limited. While the number of multi-cloning sites and the positions thereof in the exogenous gene expression vector are not particularly limited, multi-cloning sites are preferably positioned within the control region of the promoter and in the vicinity of a cassette region into which an objective gene or the like is to be incorporated. Thus, the cloned objective gene or the like can be introduced into the exogenous gene expression vector of the present aspect in a simple manner.

(4) 5' UTR and 3' UTR

5' UTR and 3' UTR are each a polynucleotide comprising a non-translational region that does not encode a protein, a fragment thereof, or a functional nucleic acid. 5' UTR and 3' UTR are selective constitutive elements in the exogenous gene expression vector of the present aspect. 5' UTR and 3' UTR are composed of nucleotide sequences provided upstream of the initiation codon (closer to the 5' terminus) and downstream of the termination codon (closer to the 3' terminus) in the mRNA coding region of an objective gene or the like, and 3' UTR can comprise a poly A signal.

(5) Signal Peptide DNA

Signal peptide DNA is a polynucleotide comprising a nucleotide sequence that encodes a signal peptide, and it is a selective constitutive element of the exogenous gene expression vector of the present aspect. A signal peptide is an extracellular transition signal that becomes necessary when a protein biosynthesized by expression of an objective gene or the like or a fragment thereof is secreted extracellularly. A signal peptide is generally arranged in the N-terminal side of a secretory protein, and it is cleaved and removed by a signal peptidase prior to secretion. When a protein of interest or a peptide fragment thereof has a signal peptide in the exogenous gene expression vector of the present aspect, accordingly, such signal peptide is arranged in the N-terminal side of a protein of interest or a peptide fragment thereof. A signal peptide generally comprises positively charged amino acids, such as Lys and Arg, on the N terminal side and highly hydrophobic amino acid sequences, such as Ala, Leu, Val, Ile, Val, and Phe, subsequent thereto. A signal peptide can also comprise an amino acid sequence comprising a signal sequence post-insertion sequence that accelerates cleavage and secretion of signal peptide and/or a signal peptidase recognition site that cleaves a signal peptide from a fusion protein at its C terminus. The amino acid sequence of a signal peptide is not particularly limited. In general, such sequence preferably comprises 3 to 60 amino acids. Accordingly, the number of nucleotides constituting whole signal peptide DNA may be 9 to 180.

Examples of signal peptide DNAs in the exogenous gene expression vector of the present aspect include, but are not limited to, signal peptide DNA encoding a sericin 1 signal peptide of silkworm comprising the amino acid sequence shown in SEQ ID NO: 6 (e.g., DNA comprising the nucleotide sequence shown in SEQ ID NO: 7), signal peptide DNA encoding a sericin 2 signal peptide of *Bombyx mori* comprising the amino acid sequence shown in SEQ ID NO: 8 (e.g., DNA comprising the nucleotide sequence shown in SEQ ID NO: 9), and signal peptide DNA encoding a sericin 3 signal peptide of silkworm comprising the amino acid sequence shown in SEQ ID NO: 10 (e.g., DNA comprising the nucleotide sequence shown in SEQ ID NO: 11).

(6) Terminator

A terminator is a selective constitutive element comprising a nucleotide sequence that can terminate the transcription of an objective gene or the like when it is expressed in the exogenous gene expression vector of the present aspect.

(7) Marker Gene

A marker gene is a polynucleotide comprising a nucleotide sequence that encodes a marker protein, which is also referred to as a "selection marker." A marker gene is a selective constitutive element of the exogenous gene expression vector of the present aspect. Examples of marker proteins include enzymes, fluorescent proteins, pigment synthetic proteins, and photoproteins. Since constitutions of such marker genes and marker proteins are described in detail in the second aspect, the description thereof is omitted herein.

(8) Insulator

An insulator is a selective constitutive element of the exogenous gene expression vector of the present aspect, and it comprises a nucleotide sequence that can stably control transcription of a gene sandwiched by sequences thereof without being influenced by a chromatin of the chromosome in the vicinity thereof. Examples thereof include a chicken cHS4 sequence and a *Drosophila* gypsy sequence.

(9) Inverted Terminal Repeat Sequence of Transposon

An "inverted terminal repeat sequence of a transposon" is a selective constitutive element that can be included when the exogenous gene expression vector of the present aspect is an expression vector capable of homologous recombination. In general, two inverted terminal repeat sequences are used in combination, and examples of transposons that can be used include piggyBac, mariner, and minos (Shimizu, K. et al., 2000, Insect Mol. Biol., 9, 277-281 and Wang, W. et al., 2000, Insect Mol. Biol., 9 (2): 145-55).

(10) Gene Expression Vector

Various types of gene expression vectors can be used as the exogenous gene expression vectors of the present aspect. Examples thereof include expression vectors capable of autonomous replication, such as plasmid and Bacmid vectors, virus vectors, expression vectors that can be homologously recombined in chromosomes, and parts of genomes into which the expression vectors described above have been introduced at its genomes. An expression vector can be a shuttle vector capable of replication in other bacteria, such as *E. coli*.

1-3. Applications

The exogenous gene expression vector of the present aspect can be used for transformation through introduction of an objective gene or the like into an insect cell, so as to express the objective gene or the like in such insect cell.

Insect species into which the exogenous gene expression vector of the present aspect is to be introduced are not limited. Examples thereof include insects belonging to Lepidoptera, Coleoptera, Hymenoptera, Hemiptera, Thysanoptera, Orthoptera, Neuroptera, and Trichoptera. Industrially applicable insects are preferable. The term "industrially applicable insects" refers to insects that are useful in human society. Examples thereof include silk-spinning insects that provide silk threads, insects of Apidae that provide honey or royal jelly, insects of *Laccifer lacca* that provide shellac, insects belonging to Apidae that are useful for pollination, and predatory insects belonging to Anthocoridae or Coccinellidae that can be used for biotic pesticides. The term "silk-spinning insects" used herein collectively refers to insects having silk glands and capable of spinning silk threads. Such term generally refers to insects capable of spinning threads for nest building, cocoon spinning, or migration at the larval stage. Specific examples include those belonging to Lepidoptera, Hymenoptera, Neuroptera, and Trichoptera. Species belonging to the order Lepidoptera that can spin large quantities of silk threads are preferable. Silk-spinning insects of species belonging to, for example, Bombycidae, Saturniidae, Brahmaeidae, Eupterotidae, Lasiocampidae, Psychidae, Archtiidae, and Noctuidae are preferable herein. Silk-spinning insects of species belonging to *Bombyx, Sarnia, Antheraea, Saturnia, Attacus*, and *Rhodinia*, more specifically, *Bombyx mori, Bombyx mandarina, Samia cynthia* (including *Samia cynthia ricini* and a crosshybrid of *Samia cynthia* and *Samia cynthia ricini*), *Antheraea yamamai, Antheraea pernyi, Saturnia japonica*, and *Actias gnoma* are more preferable. In addition to the industrial applicability, insects with limited mobility and/or insects that can be grown in a closed space are particularly preferable as insects into which the gene expression vector of the present aspect is to be introduced. A typical example is silkworm *Bombyx mori*.

1-4. Method of Introduction

A method for introducing the exogenous gene expression vector of the present aspect is described.

A host into which the exogenous gene expression vector of the present aspect is to be introduced may be an insect-derived cell (including a cell line), insect-derived tissue, or insect body. A cell or tissue may be collected or derived from an insect at any developmental stage. For the same reason, the developmental stage of an insect is not limited, and it may be any of the embryonic, larval, pupa, and adult stages. A host may be male or female.

An exogenous gene expression vector may be introduced into a host in accordance with the type of the exogenous gene expression vector by a method known in the art. When a host is silkworm and an exogenous gene expression vector is a plasmid comprising inverted terminal repeat sequences of a transposon (Handler, A. M. et al., 1998, Proc. Natl. Acad. Sci., U.S.A., 95: 7520-5), for example, the method of Tamura et al. can be adopted (Tamura, T. et al., 2000, Nature Biotechnology, 18, 81-84). In short, the exogenous gene expression vector of the present aspect may be injected into an early embryo of silkworm together with a helper vector comprising DNA that encodes transposase. An example of the helper vector is pHA3PIG. When the exogenous gene expression vector of the present aspect comprises a marker gene as an objective gene or the like, a transformant can be easily selected on the basis of expression of such gene or the like (which is described in detail in the second aspect).

1-5. Effects

Through introduction of the exogenous gene expression vector of the present aspect into an insect cell, objective gene expression can be strongly induced throughout the body at any developmental stage from the embryo to adult.

2. Transformant Discrimination Marker 2-1 Summary

The second aspect of the present invention concerns a transformant discrimination marker. An insect into which the transformant discrimination marker of the present aspect has been introduced; that is, a transformant, can be easily identified at an early embryonic stage.

2-2. Constitution

The constitution of the transformant discrimination marker of the present aspect of the present invention is the same as that of the exogenous gene expression vector of the first aspect. The exogenous gene expression vector of the first aspect can comprise an objective gene or the like that can encode a protein of interest or a peptide fragment thereof. In the transformant discrimination marker of the present aspect, however, the objective gene or the like of the exogenous gene expression vector of the first aspect is limited to a marker gene or a functional nucleotide fragment thereof. Specifically, the transformant discrimination marker of the present aspect can be regarded as an embodiment of the exogenous gene expression vector of the first aspect. Since the basic constitution of the transformant discrimination marker of the present aspect is in common with that of the exogenous gene expression vector of the first aspect, the constitution characteristic of the present aspect is specifically described herein.

(1) Marker Gene

The term "marker gene" used herein refers to a gene encoding a marker protein. The term "marker protein" used herein refers to a polypeptide that can determine whether or not the marker gene is expressed on the basis activity thereof. On the basis of activity of the marker protein, accordingly, a transformant having the transformant discrimination marker of the present aspect can be easily identified. Here, the phrase "on the basis of its activity" means "on the basis of the results of detection of activity". When detecting activity, activity of the marker protein may be directly detected, or it may be indirectly detected through a metabolite generated by activity of a marker protein such as a pigment. Detection may be carried out by means of chemical detection (including detection via enzyme reaction), physical detection (including detection via behavior analysis), or sensory detection by a detector (including detection based on visual perception, touch, olfactory perception, auditory perception, and taste sensation).

A marker protein type is not particularly limited, provided that activity thereof can be detected by a method known in the art. A marker protein exhibiting a low invasiveness at the time of detecting a host that carries a transformant discrimination marker; i.e., a transformant, is preferable. Examples thereof include a fluorescent protein, a pigment synthetic protein, a photoprotein, an excretory-secretory protein, and a protein that controls an external configuration. A fluorescent protein, a pigment synthetic protein, a photoprotein, and an excretory-secretory protein enable visual detection under particular conditions without changing an external configuration of a transformant Thus, such proteins are particularly preferable in terms of very low invasiveness to a transformant and ease of identification and selection of a transformant The term "fluorescent protein" used herein refers to a protein that emits a fluorescence of a particular wavelength when irradiated with an excitation light of a particular wavelength. It may be a naturally-occurring or non-naturally-occurring protein. The excitation wavelength and the fluorescence wavelength are not particularly limited. Specific examples include CFP, RFP, DsRed (including a derivative such as 3×P3-DsRed), YFP, PE, PerCP, APC, and GFP (including derivatives such as EGFP and 3×P3-EGFP).

The term "pigment synthetic protein" used herein refers to a protein that is associated with biosynthesis of a pigment, and it is generally an enzyme. The term "pigment" used herein refers to a low-molecular-weight compound or peptide that can confer the pigment on a transformant, and a type thereof is not limited. A pigment appearing as an exterior color of an individual is preferable. Examples thereof include a melanin pigment (including dopamine melanin), an ommochrome pigment, and a pteridine pigment.

The term "photoprotein" used herein refers to a substrate protein that can emit light without excitation light, or an enzyme that catalyzes luminescence of such substrate protein. Examples thereof include substrate proteins, such as luciferin and aequorin, and an enzyme, such as luciferase.

The term "excretory-secretory protein" used herein refers to a protein that is excreted extracellularly or extracorporeally. In addition to exocrine enzymes, fibrous proteins, such as fibroin, and sericin are regarded as "excretory-secretory proteins." Examples of exocrine enzymes include an enzyme that contributes to degradation or inactivation of a drug such as blasticidin and imparts a host with drug resistance and a digestive enzyme.

A marker gene is located expressibly downstream of a promoter in the transformant discrimination marker.

(2) Functional Nucleotide Fragment

As with the case of the marker gene, a functional nucleotide fragment is located expressibly downstream of a promoter in the transformant discrimination marker.

The term "functional nucleotide fragment (thereof)" used herein refers to a fragment of a marker gene and a nucleotide encoding a functional peptide fragment. The term "functional peptide fragment" refers to a fragment of a marker protein, and it is a peptide carrying the activity thereof. The number of amino acids constituting a functional peptide fragment is not limited, provided that activity of the marker protein is retained.

(3) Others

The transformant discrimination marker of the present aspect may comprise two or more marker genes and/or functional nucleotide fragments within the control region of the promoter of the first aspect. In such a case, marker genes and functional nucleotides may encode a marker protein having the same activity or different marker proteins each having different activity. For example, the transformant discrimination marker may comprise two genes encoding a fluorescent protein (i.e., GFP), or it may comprise a gene encoding GFP in combination with a gene encoding a pigment synthetic protein. In the case of the former, advantageously, the expression level of marker proteins relative to a transformant discrimination marker can be doubled, and sensitivity for identifying a transformant can be enhanced. In the case of the latter, a transformant can be detected based on two different perspectives; i.e., fluorescence and color. Thus, the accuracy for identification can be advantageously enhanced.

The transformant discrimination marker of the present aspect can comprise the objective protein of the first aspect, a peptide fragment thereof, or a polynucleotide encoding a functional nucleic acid within the promoter control region, in addition to the marker genes and/or functional nucleotide fragments. When a mutant protein is expressed throughout an insect body and functional analysis thereof is intended, for example, a transformant discrimination marker comprising such mutant protein and a gene encoding a marker protein within the promoter control region may be introduced into an insect body. The identification of a transformant with the marker protein and the functional analysis of the mutant protein throughout the insect body can be performed simultaneously.

2-3. Effects

According to the transformant discrimination marker of the present aspect, when it is introduced into a host insect, marker genes that are present or functional nucleotide fragments thereof throughout the host insect body can be strongly expressed therein throughout all developmental stages from the embryo to the adult. Thus, a transformant can be easily identified even with the use of an embryo at the early developmental stage, which was difficult to identify according to a conventional technique.

3. Transformant 3-1 Summary

The third aspect of the present invention concerns a transformant. The transformant of the present aspect comprises the exogenous gene expression vector of the first aspect or the transformant discrimination marker of the second aspect. The transformant of the present aspect is capable of expressing objective genes or the like contained in the exogenous gene expression vector of the first aspect or the transformant discrimination marker of the second aspect in the whole body at any developmental stage.

3-2. Constitution

The transformant of the present aspect comprises the exogenous gene expression vector of the first aspect or the transformant discrimination marker of the second aspect in a cell. Specifically, a host transformed by the introduction of the exogenous gene expression vector of the first aspect or the transformant discrimination marker of the second aspect correspond to the transformant of the present aspect. As described above, the basic constitution of the transformant discrimination marker of the second aspect is the same as that of the exogenous gene expression vector of the first aspect, and the transformant discrimination marker of the second aspect can be regarded as an embodiment of the exogenous gene expression vector of the first aspect. In the present aspect, accordingly, the transformant discrimination marker of the second aspect is included in the exogenous gene expression vector of the first aspect. Thus, the transformant of the present aspect is composed of a host and the exogenous gene expression vector of the first aspect. Hereafter, the transformant of the present aspect is described in detail.

(1) Host

Hosts constituting the transformant of the present aspect are the same as the insects described in "1-3. Applications" in the first embodiment. While the insect species is not limited, industrially applicable insects are preferable, and insects with limited mobility and/or insects that can be grown in a closed space are more preferable. An example of a preferable host is silkworm. The conditions of the host are the same as those of the hosts described in "1-4. Method of introduction." Specifically, hosts are insect-derived cells (including established cells), insect-derived tissue, or insect bodies. Types, developmental stages, and sexuality thereof are not particularly limited.

In addition to the first-generation transformants into which the exogenous gene expression vector of the first aspect has been introduced, progenies thereof are within the scope of the hosts. The term "progeny" used herein refers to an individual offspring of the first generation of a transformant, which carries the exogenous gene expression vector of the first aspect in its cell. The generation of the progeny is not particularly limited, provided that it carries the exogenous gene expression vector of the first aspect.

(2) The Exogenous Gene Expression Vector of the First Aspect

Since the specific constitution of the exogenous gene expression vector of the first aspect is described in detail in the first aspect, the description thereof is omitted herein.

The exogenous gene expression vector of the first aspect can be integrated into the genome of the host cell. Alternatively, it can be present independent of the host genome. When the exogenous gene expression vector is independent of the host genome, the existence of such vector may be transient in the host cell. In such a case, the existence of the transformant of the present aspect is temporary or limited to the present generation. In order to stably and continuously maintain the transformant of the present aspect, the exogenous gene expression vector of the first aspect is preferably integrated into the host genome.

Example 1: Preparation of Silkworm (*Bombyx mori*) Transformant Comprising Exogenous Gene Expression Vector (Objectives)

It was found that a reporter gene inserted under the control of the hsp90 gene promoter would strongly induce expression throughout the body from the embryonic stage to the adult stage of silkworm in the silkwormAyFib-431a line isolated from the enhancer trap system. As the exogenous gene expression vector of the present invention, accordingly, an expression vector with the hsp90 gene promoter was constructed, so as to examine whether or not such expression vector would exert the effects of the present invention.

(Method)

(1) Construction of Exogenous Gene Expression Vector

First, the pBacA3dGAL4/3×P3DsRed (ANB) vector was prepared by substituting the BamHI site of the pBacA3dGAL4/3×P3DsRed vector (Uchino, K. et al., 2006, J. Insect Biotechnol. Sericol., 75: 89-97) with the NheI site. The resulting vector was cleaved with AscI and XbaI, the A3dGAL4 fragment was removed, and the GFP and the SV40 terminator sequence amplified via PCR were inserted thereinto, so as to prepare the pBacGFP/3×P3DsRed vector.

Next, a region of about 2.9 kb upstream from the transcription initiation site of the silkworm hsp90 gene (g2900: 2,884 bp) was designated as the candidate region of the hsp90 gene promoter, and this region was amplified via PCR using the forward primer (SEQ ID NO: 12) and the reverse primer (SEQ ID NO: 13) and the genome of the silkworm white/C line as a template. KOD plus (Toyobo Co., Ltd.) was used as DNA polymerase. PCR was carried out through thermal denaturation at 94° C. for 5 minutes, followed by a cycle of 94° C. for 30 seconds, 60° C. for 30 seconds, and 68° C. for 3 minutes, which was repeated 35 times. The amplified product was inserted and cloned into the pCR-BluntII-TOPO vector (Life Technologies) to obtain pCR-BluntII-g2900. The nucleotide sequence of the cloned region was checked via sequencing, and PCR was carried out with the use of pCR-BluntII-g2900 as a template and the forward primer (SEQ ID NO: 14) and the reverse primer (SEQ ID NO: 15), comprising the NheI site at the 5' terminus, so as to amplify the g2900 sequence again.

Figure 3:
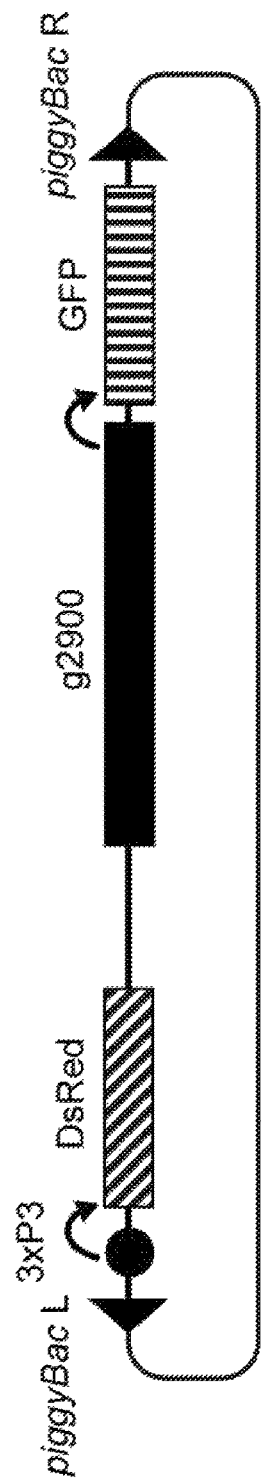
FIG. 3 shows an embodiment of the exogenous gene expression vector according to the present invention prepared in Example 1. The exogenous gene expression vector shown in FIG. 3 comprises g2900 comprising the nucleotide sequence shown in SEQ ID NO: 4, which is derived from the hsp90 gene promoter of silkworm and a GFP gene ligated thereto.

The re-amplified fragment was inserted into the XbaI site located upstream of the GFP gene of the pBacGFP/3× P3DsRed vector, and the exogenous gene expression vector of the present invention shown in FIG. 3 (i.e., the transformation discrimination marker) was obtained (pBacg2900GFP/3×P3DsRed).

(2) Purification of Exogenous Gene Expression Vector

The constructed exogenous gene expression vector was purified using the HiSpeed Plasmid Midi Kit (Qiagen) in accordance with the protocols included in the kit. The expression vector was further purified via phenol/chloroform extraction and ethanol precipitation, and the resultant was dissolved in 0.5 mM phosphate buffer (pH 7.0)/5 mM potassium chloride buffer.

(3) Preparation of Transgenic Silkworm

The exogenous gene expression vector pBacg2900GFP/ 3×P3DsRed constructed above was mixed with the transposase-expressing helper plasmid pHA3PIG (Tamura, T. et al., 2000, Nature Biotechnology, 18, 81-84) at 1:1, and the resultant was injected into the embryos of the silkworm w1-pnd line (a non-diapausing line characterized by white eyes and white eggs) 2 to 8 hours after egg-deposition. The pores created on the embryos after the injection were sealed with the use of an instant adhesive (#30523, Konish), and incubation was carried out under humidified conditions at 25° C. until hatching occurred. The hatched larvae were raised and the resulting adults were crossed by sib mating or with un-injected individuals. The embryos were selected in accordance with the expression of 3×P3DsRed, and the transgenic silkworm line of the third aspect comprising the exogenous gene expression vector was obtained.

In order to confirm the promoter activity of g2900 in the obtained transgenic silkworm line comprising the exogenous gene expression vector of the present invention, expression of the GFP gene ligated to the downstream of g2900 was confirmed on the basis of GFP fluorescence. GFP fluorescence was observed under the fluorescence stereoscopic microscope (MZ16FA, Leica).

(Results)

The results are shown in FIG. 4. As with the case of the original AyFib-431a line, it was demonstrated that the exogenous gene expression vector of the present invention comprising g2900 could strongly induce expression of the GFP gene in the control region throughout the whole body at any developmental stage from the embryo to the adult could exert the effects of the present invention.

Example 2: Determination of Active Region of Silkworm Hsp90 Gene Promoter (Objectives)

The results of Example 1 suggest that g2900 has hsp90 gene promoter activity of silkworm. In this example, accordingly, the minimal active region of the hsp90 gene promoter that can function as a promoter of the exogenous gene expression vector of the present invention was determined on the basis of g2900.

(Method)

(1) Construction of Exogenous Gene Expression Vector

Figure 5A:
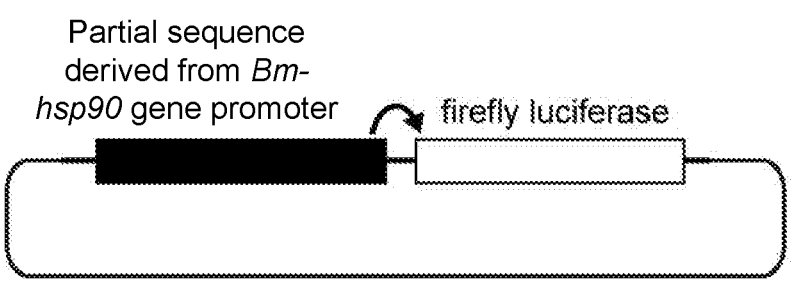
FIG. 5 shows the expression vector used in Example 3. A shows an expression vector having the constitution of the exogenous gene expression vector of the present invention comprising a partial sequence derived from the hsp90 gene promoter of silkworm (Bm-hsp90) and firefly luciferase ligated thereto. A partial sequence derived from the hsp90 gene promoter in this expression vector is replaced with partial sequences of various lengths shown in FIG. 6, so as to examine promoter activity of partial sequences shown in FIG. 7. B shows a correction vector comprising the immediate-early 2 (IE2) gene promoter of *Orgyia pseudotsugata* and *Renilla* luciferase logated thereto.

In order to assay the promoter activity of the g2900 sequence or a partial sequence thereof, an exogenous gene expression vector was constructed by inserting promoter sequences into the upstream of the luciferase gene of the firefly-derived luminescent enzyme protein shown in FIG. 5A.

The exogenous gene expression vector into which the full-length g2900 sequence had been inserted was constructed by performing PCR with the use of the forward primer (SEQ ID NO: 14) and the reverse primer (SEQ ID NO: 15) and pCR-BluntII-g2900 prepared in Example 1 as a template, so as to prepare the g2900 sequence, and inserting the resulting amplified fragment into the NheI/XhoI site of the pGL3 vector (Promega). The resultant was designated as pGL3-g2900.

Figure 6:
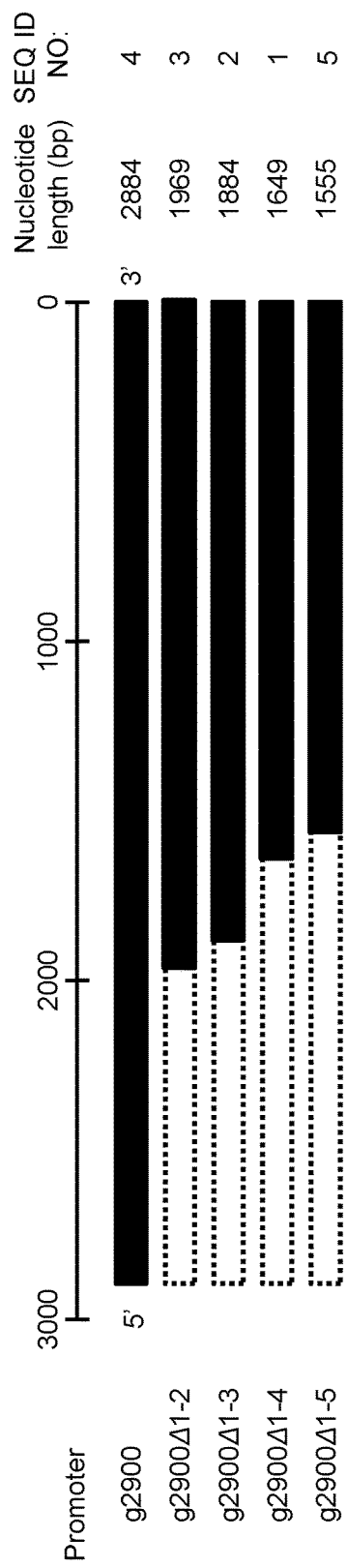
FIG. 6 shows partial sequences of various lengths derived from the silkworm hsp90 gene promoter used for the expression vector shown in FIG. 5A. g2900 has the maximal length, and other promoters were prepared by deleting regions closer to the 5' ends (regions indicated with broken lines).

With regard to each of the exogenous gene expression vectors into which any of the partial sequences of the hsp90 gene promoters shown in FIG. 6 (i.e., g2900Δ1-2, g2900Δ1-3, g2900Δ1-4, and g2900Δ1-5) had been inserted, an upstream region (2033 bp) of the XbaI site (i.e., a region from the 5' terminus up to position 2033 of g2900) was amplified by PCR. Specifically, the forward primers specific for each partial fragment (g2900Δ1-2: SEQ ID NO: 16, g2900Δ1-3: SEQ ID NO: 17, g2900Δ1-4: SEQ ID NO: 18, or g2900Δ1-5: SEQ ID NO: 19) and the reverse primer (SEQ ID NO: 20) common for all partial fragments were used. The amplified products were inserted into pCR-BluntII, and the nucleotide sequences of the cloned regions were checked via sequencing. pGL3-g2900 was cleaved with XbaI to obtain a fragment containing a region following the position 2033 of g2900, and the resulting fragment was inserted into the XbaI site of each plasmid. Thus, pCR-BluntII-g2900Δ1-2, pCR-BluntII-g2900Δ1-3, pCR-BluntII-g2900Δ1-4, and pCR-BluntII-g2900Δ1-5 were obtained. These plasmids were cleaved with NheI and XhoI to cleave g2900 partial sequences, and the partial sequences were inserted into pGL3. Thus, pGL3-g2900Δ1-2, pGL3-g2900Δ1-3, pGL3-g2900Δ1-4, and pGL3-g2900Δ1-5 were prepared.

(2) Purification of Exogenous Gene Expression Vector

As in the case of Example 1, the constructed exogenous gene expression vectors were purified using the HiSpeed Plasmid Midi Kit (Qiagen) in accordance with the protocols included in the kit. The expression vectors were further purified via phenol/chloroform extraction and ethanol precipitation, and the resultants were dissolved in 0.5 mM phosphate buffer (pH 7.0)/5 mM potassium chloride buffer.

(3) Correction Vector

Figure 5B:
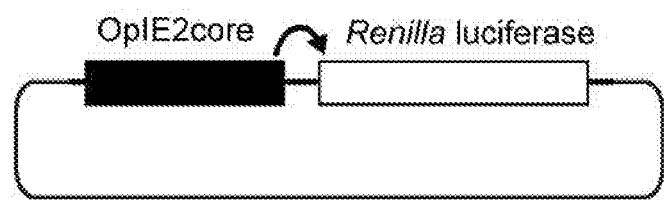

As a correction vector used for correcting the efficiency of gene introduction into culture cells, the pOpIE2-core-Rluc vector expressing *Renilla* luciferase (Rluc) under the control of the immediate-early 2 (IE2) gene promoter of the tussock moth *Orgyia pseudotsugata* shown in FIG. 5B was used (Tanaka, et al., 2012, Insect Biochem. Mol. Biol., 42, 474-481).

(4) Transfection into Cells for Silkworm Culture

NIAS-Bm-oyanagi2 cells (obtained from the National Institute of Agrobiological Sciences (NIAS)) were used for silkworm culture. Fugene (1.6 Promega), 0.1 µg each of exogenous gene expression vectors, and 0.1 µg of the pOpIE2-core-Rluc control vector were mixed, the mixture was transfected into the $4.5 \times 10^4$ Oyanagi cells. Following incubation at 25° C. for 72 hours, the cells were lysed using 5× Passive Lysis Buffer (Promega) and stored at −80° C.

(5) Luciferase activity assay

Firefly luciferase activity and *Renilla* luciferase activity were assayed using the dual-luciferase assay system (Promega). A suspension of the luciferase assay substrate in luciferase assay buffer II was added to the cell lysis solution obtained in (4), and activity of firefly luciferase (Luc) was assayed using a luminometer (Nichion). Thereafter, a suspension of Stop & Glo Substrate in Stop & Glo Buffer was added, and activity of *Renilla* luciferase (Rluc) was assayed. On the basis of the assayed *Renilla* luciferase activity, firefly luciferase activity derived from each exogenous gene expression vector was corrected, and promoter activity of each hsp90 partial fragment was determined.

(Results)

Figure 7:
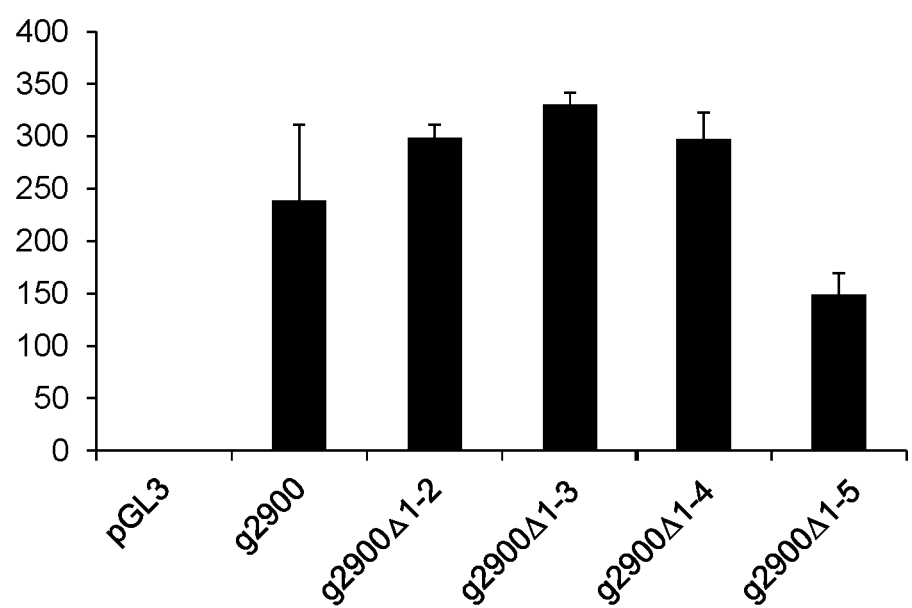
FIG. 7 shows the results obtained by introducing the two expression vectors shown in FIGS. 5A and 5B into silkworm culture cells, assaying the luciferase expression levels, and correcting the firefly luciferase expression levels with the *Renilla* luciferase expression levels (i.e., relative value which is the firefly luciferase activity relative to the *Renilla* luciferase activity (Luc/Rluc)). pGL3 is a control vector that does not comprise a promoter sequence.

The results are shown in FIG. 7. Firefly luciferase activity was observed at high levels in g2900Δ1-2, g2900Δ1-3, and g2900Δ1-4, and promoter activity was found to be equivalent to or stronger than that of g2900. In addition, the promoter activity of g2900Δ1-3 shown in SEQ ID NO: 2 was found to be the strongest among the promoters described above.

In contrast, although g2900Δ1-5 shown in SEQ ID NO: 5 having a sequence of 1555-bp upstream from the transcription initiation site was found to have promoter activity, it was significantly lower than that of other partial sequences.

The results described above demonstrate that g2900Δ1-4, which is a region of 1649 bp upstream from the transcription initiation site of the hsp90 gene of silkworm shown in SEQ ID NO: 1, was found to have activity necessary and sufficient as a promoter required for the exogenous gene expression vector according to the present invention.

Example 3: Comparison of Gene Promoter Activity (Objectives)

Activity of the silkworm hsp90 gene promoter for inducing gene expression was compared with that of a conventional gene promoter, which had been often used.

(Method)

(1) Construction and Purification of Exogenous Gene Expression Vector

Methods of construction and purification of exogenous gene expression vectors were basically in accordance with those described in Example 1. g2900 was used as the hsp90 gene promoter of silkworm. The pGL3 vector (Promega) was used as a negative control. The actin A3 gene promoter (BmA3) often used as a gene promoter for gene recombination of silkworm was used as a control promoter for activity comparison. As the exogenous gene expression vector into which g2900 had been introduced, pGL3-g2900 prepared in Example 2 was used. Meanwhile, the exogenous gene expression vector pGL3-BmA3 into which BmA3 had been introduced was prepared in the manner described below. Firstly, PCR was carried out using the pHA3PIG vector described in Tamura, T. et al., 2000, Nat. Biotechnol., 18: 81-84 as a template and the forward primer comprising the NheI site at the 5' terminus (CTAGCTAGCCCGGGCTCAAGCTTGATGCG: SEQ ID NO: 21) and the reverse primer comprising the XhoI site at the 5' terminus (CCGCTCGAGTGAATTAGTCTGCAAGAA: SEQ ID NO: 22), so as to amplify the BmA3 promoter region. KOD plus (Toyobo Co., Ltd.) was used as DNA polymerase. PCR was carried out through thermal denaturation at 95° C. for 1 minute, followed by a cycle of 95° C. for 30 seconds, 60° C. for 30 seconds, and 68° C. for 1 minute, which was repeated 30 times. Subsequently, the amplified product was cleaved with NheI and XhoI, and the resulting fragment was then inserted into the pGL3 vector. The resultant was designated as pGL3-BmA3.

(2) Correction Vector

The pOpIE2-core-Rluc vector described in Example 2 was used as a correction vector used for correcting the efficiency of gene introduction into culture cells.

(3) Transfection into Cells for Silkworm Culture

Transfection into silkworm culture cells was carried out in accordance with the method specifically described in Example 2.

(4) Luciferase Activity Assay

Luciferase activity assay was carried out in accordance with the method described in Example 2.

(Results)

Figure 8:
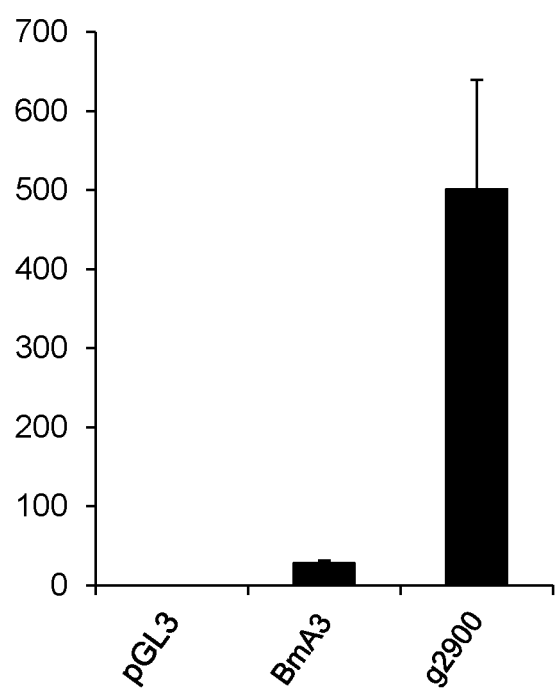
FIG. 8 shows the results of comparison of activity of g2900 derived from the silkworm hsp90 gene promoter and activity of a conventional actin A3 gene promoter of silkworm (BmA3). A vertical axis represents relative value which is the firefly luciferase activity relative to the *Renilla* luciferase activity (Luc/Rluc).

The results are shown in FIG. 8. The g2900 derived from the silkworm hsp90 gene promoter of the present invention was found to exhibit activity, which was approximately 20 times greater than that of the silkworm A3 promoter that had been generally used in the art. That is, the g2900 described above was found to be a promoter exhibiting very high activity and efficiency.

INDUSTRIAL APPLICABILITY

Through introduction of the exogenous gene expression vector according to the present invention into an insect cell, objective gene expression can be strongly induced throughout the body at any developmental stage from the embryonic to adult stages.

Through introduction of the transformant discrimination marker according to the present invention into an insect cell, a transgenic insect can be easily, efficiently, and accurately identified at any developmental stage from the embryonic to adult stages.

All publications, patents, and patent applications cited herein are incorporated herein by reference in their entirety.

The invention claimed is:

1. An expression vector comprising a cassette region for incorporating one or more objective genes,
wherein the objective genes are controlled by, and located downstream of, a promoter comprising a nucleotide sequence shown in SEQ ID NO: 1.

2. The expression vector according to claim 1, wherein the cassette region comprises one or more objective genes.

3. The expression vector according to claim 2, wherein the one or more objective genes is a marker gene encoding a protein selected from the group consisting of an enzyme, a fluorescent protein, a pigment synthetic protein, and a photoprotein.

4. A transformant comprising the expression vector according to claim 2, wherein the transformant belongs to a species of the order Lepidoptera.

5. The transformant according to claim 4, wherein the transformant genome comprises the expression vector.

6. A transformant comprising the expression vector according to claim 3, wherein the transformant belongs to a species of the order Lepidoptera.

7. The transformant according to claim 6, wherein the transformant belongs to a *Bombyx* species.

8. A method for identifying a transformant, comprising introducing an expression vector into an organism of a species of the order Lepidoptera to produce a transformant, and selecting the transformant, after the introduction step, that expresses a marker gene encoding a protein selected from the group consisting of an enzyme, a fluorescent protein, a pigment synthetic protein, and a photoprotein, wherein the expression vector comprises one or more objective genes, the marker gene, and a promoter, the promoter comprising the nucleotide sequence according to SEQ ID NO: 1, and wherein the objective genes are controlled by, and located downstream of the promoter.

9. The method for identifying a transformant according to claim 8, wherein the transformant belongs to a *Bombyx* species.

\* \* \* \* \*

SEQUENCE LISTING

```
<160> NUMBER OF SEQ ID NOS: 22

<210> SEQ ID NO 1
<211> LENGTH: 1649
<212> TYPE: DNA
<213> ORGANISM: Bombyx mori
<220> FEATURE:
<223> OTHER INFORMATION: hsp90 promoter g2900 delta 1-4

<400> SEQUENCE: 1
ttatcgggcg agtagcgcct cccaccacgc gtcctagctc actggctcac tgactaaaca      60
agtccgaacc tgttgattag tcgagttcat tagtggcgct tctcaaatgg aactttcgga     120
cattcttaaa ctatcgaagt attctttggg atctcttcca atgctaattc tttcagaaga     180
catttatctc ttcaatcgat ccattttcgt acctataact tattttcat aatcacagaa      240 atttgctcgt ccaccttttc taaaatagcc attacgatta gcttaatcag tttattcact     300
ctattgcgtt gcagtctgtt catcctgcaa aacaccactc acttgtgtac tctactggac     360
cgtaatgcga acgatttctg tgcagtagcg agtagtttag ccactaaatt actcggtact     420
cgactaaaat actcgcctag tccgaacaag gctttagcga catatttacg taacgtatac     480
accccgataa agagatttac tgtccaaaaa aaacgtcaaa aaatggaaca aattatgtgc     540
tttttattta ttggtattac taatttcgtt aagaatttca tcggaagcag ccagcgccga     600
atgcggtgaa tagtaaaact ataagaagga agcggttgga atgatctggg taaaatgtta     660
tttcttacga attacgatga ttctttgatt aaatttggaa aagtttgtg gtcaaattat      720 ttaacattca tcttgtatca tttattgact ctaatttcaa ctaagttatt tctgtaatgt     780
taaaatttcg atgcttttct agaatattca ggaatgttcc agatattctt gtgtgtagat     840
cgtattgcca ccttgtgcca aatagcggca ctaaaataat tcggcagagc tatacaacat     900
ttggtaattt tatttatttt gctatttttcc ccagttttttt aaattactgt gttttttaact     960 agcaattaca tttaattgga tgcaatttac actgccttaa taattttttt ttagttgtaa    1020
tttggtttct tacgtttatg ctgtatattt ttagtgatct gcaaaatgcg aaacactgaa    1080
cagcttagga aaatttaaaa tgtgagatgt ttcttttact taaataaata cttaaaatat    1140
aacagagaaa aaacatttttt aactagtctg gcatatttta gtgaatctat tgatgaaaat    1200
gaacgaaata tgtaattacc tttataattt cttgaattat tttaaggaaa tatattttc     1260 ctaacacttt aaacttcaaa gcgggtgatg caataataac taacacaaaa agaaacttgc    1320
agtgttaagt aaatgatttt tctcttcgtt ttatggcctc ccaaaatgaa ataattgcca    1380
attaatttga aatgattaat tatttttatt taatattgtt tcggtttgta ttgatggtaa    1440
aatgttgatg ctctctgacg gaaatagcgt cagaatcgag aaacttctac tgattcatag    1500
atgtcgcttg ctagaggaaa gtataaaaac gaatttacac accgcgcccg gcgttatttg    1560
aactaagaga agtacggaga ctaacgtttg atactttgcg ctttgaaaca cgtgtgttaa    1620
```

```
aaacccctcta gtcatttgt gtgaattaa                                      1649
```

<210> SEQ ID NO 2
<211> LENGTH: 1884
<212> TYPE: DNA
<213> ORGANISM: Bombyx mori
<220> FEATURE:
<223> OTHER INFORMATION: hsp90 promoter g2900 delta 1-3

<400> SEQUENCE: 2

```
cgcggatcta atcgatacat agacattgat aaaagaaat ccaatattaa gtattcaact        60
gaatatcctt tataatcgcg ctataatcac ggtttatcta taaagccttg ttcggactag      120
gcgagtattt tagtcgagta ccgagtaatt tagtagctaa atgtgtccga gcaccaaaag      180
tttagtcgag taggttagta aataatttag taaagccaat ccattttgtt ctattttatc      240
gggcgagtag cgcctcccac cacgcgtcct agctcactgg ctcactgact aaacaagtcc      300
gaacctgttg attagtcgag ttcattagtg gcgcttctca aatggaactt tcggacattc      360
ttaaactatc gaagtattct ttgggatctc ttccaatgct aattctttca gaagacattt      420
atctcttcaa tcgatccatt ttcgtaccta taacttattt ttcataatca cagaaatttg      480
ctcgtccacc ttttctaaaa tagccattac gattagctta atcagtttat tcactctatt      540
gcgttgcagt ctgttcatcc tgcaaaacac cactcacttg tgtactctac tggaccgtaa      600
tgcgaacgat ttctgtgcag tagcgagtag tttagccact aaattactcg gtactcgact      660
aaaatactcg cctagtccga acaaggcttt agcgacatat ttacgtaacg tatacacccc      720
gataaagaga tttactgtcc aaaaaaaacg tcaaaaaatg gaacaaatta tgtgcttttt      780
atttattggt attactaatt tcgttaagaa tttcatcgga agcagccagc gccgaatgcg      840
gtgaatagta aaactataag aaggaagcgg ttggaatgat ctgggtaaaa tgttatttct      900
tacgaattac gatgattctt tgattaaatt tggaaaagtt ttgtggtcaa attatttaac      960
attcatcttg tatcatttat tgactctaat ttcaactaag ttatttctgt aatgttaaaa     1020
tttcgatgct tttctagaat attcaggaat gttccagata ttcttgtgtg tagatcgtat     1080
tgccaccttg tgccaaatag cggcactaaa ataattcggc agagctatac aacatttggt     1140
aattttatt atttttgctat ttttccccagt ttttttaaatt actgtgtttt taactagcaa    1200
ttacatttaa ttggatgcaa tttacactgc cttaataatt tttttttagt tgtaatttgg     1260
tttcttacgt ttatgctgta tatttttagt gatctgcaaa atgcgaaaca ctgaacagct     1320
taggaaaatt taaatgtga gatgtttctt ttacttaaat aaatacttaa aatataacag     1380
agaaaaaaca tttttaacta gtctggcata ttttagtgaa tctattgatg aaaatgaacg     1440
aaatatgtaa ttacctttat aatttcttga attattttaa ggaaatatat ttttcctaac    1500
actttaaaact tcaaagcggg tgatgcaata ataactaaca caaaagaaa cttgcagtgt     1560
taagtaaatg atttttctct tcgttttatg gcctcccaaa atgaaataat tgccaattaa     1620
tttgaaatga ttaattattt ttatttaata ttgtttcggt ttgtattgat ggtaaaatgt     1680
tgatgctctc tgacggaaat agcgtcagaa tcgagaaact tctactgatt catagatgtc    1740
gcttgctaga ggaaagtata aaaacgaatt tacacaccgc gcccggcgtt atttgaacta    1800
agagaagtac ggagactaac gtttgatact ttgcgctttg aaacacgtgt gttaaaaacc    1860
ctctagtcat tttgtgtgaa ttaa                                            1884
```

<210> SEQ ID NO 3
<211> LENGTH: 1969

<212> TYPE: DNA
<213> ORGANISM: Bombyx mori
<220> FEATURE:
<223> OTHER INFORMATION: hsp90 promoter g2900 delta 1-2

<400> SEQUENCE: 3

```
tcgcgtttcc ttcactcgcg ttttcactat tcgcagatta aaatgtgtcc caattcctat    60
tttcgcaatt aaagatctct ttattcgcgg atctaatcga tacatagaca ttgataaaaa   120
gaaatccaat attaagtatt caactgaata tcctttataa tcgcgctata atcacggttt   180
atctataaag ccttgttcgg actaggcgag tattttagtc gagtaccgag taatttagta   240
gctaaatgtg tccgagcacc aaaagtttag tcgagtaggt tagtaaataa tttagtaaag   300
ccaatccatt ttgttctatt ttatcgggcg agtagcgcct cccaccacgc gtcctagctc   360
actggctcac tgactaaaca agtccgaacc tgttgattag tcgagttcat tagtggcgct   420
tctcaaatgg aactttcgga cattcttaaa ctatcgaagt attctttggg atctcttcca   480
atgctaattc tttcagaaga catttatctc ttcaatcgat ccattttcgt acctataact   540
tatttttcat aatcacagaa atttgctcgt ccaccttttc taaaatagcc attacgatta   600
gcttaatcag tttattcact ctattgcgtt gcagtctgtt catcctgcaa acaccactc    660
acttgtgtac tctactggac cgtaatgcga acgatttctg tgcagtagcg agtagtttag   720
ccactaaatt actcggtact cgactaaaat actcgcctag tccgaacaag gctttagcga   780
catatttacg taacgtatac accccgataa agagatttac tgtccaaaaa aaacgtcaaa   840
aaatggaaca aattatgtgc ttttttattta ttggtattac taatttcgtt aagaatttca   900
tcggaagcag ccagcgccga atgcggtgaa tagtaaaact ataagaagga agcggttgga   960
atgatctggg taaatgttta tttcttacga attacgatga ttctttgatt aaatttggaa  1020
aagttttgtg gtcaaattat ttaacattca tcttgtatca tttattgact ctaatttcaa  1080
ctaagttatt tctgtaatgt taaaatttcg atgcttttct agaatattca ggaatgttcc  1140
agatattctt gtgtgtagat cgtattgcca ccttgtgcca aatagcggca ctaaaataat  1200
tcggcagagc tatacaacat ttggtaattt tatttatttt gctatttcc  ccagtttttt  1260
aaattactgt gtttttaact agcaattaca tttaattgga tgcaatttac actgccttaa  1320
taattttttt ttagttgtaa tttggttttct tacgtttatg ctgtatattt ttagtgatct  1380
gcaaaatgcg aaacactgaa cagcttagga aaatttaaaa tgtgagatgt ttcttttact  1440
taaataaata cttaaaatat aacagagaaa aaacattttt aactagtctg gcatattta   1500
gtgaatctat tgatgaaaat gaacgaaata tgtaattacc tttataattt cttgaattat  1560
tttaaggaaa tatatttttc ctaacacttt aaacttcaaa gcgggtgatg caataataac  1620
taacacaaaa agaaacttgc agtgttaagt aaatgatttt tctcttcgtt ttatggcctc  1680
ccaaaatgaa ataattgcca attaatttga aatgattaat tattttttatt taatattgtt  1740
tcggtttgta ttgatggtaa aatgttgatg ctctctgacg gaaatagcgt cagaatcgag  1800
aaacttctac tgattcatag atgtcgcttg ctagaggaaa gtataaaaac gaatttacac  1860
accgcgcccg gcgttatttg aactaagaga agtacggaga ctaacgtttg atactttgcg  1920
cttttgaaaca cgtgtgttaa aaaccctcta gtcattttgt gtgaattaa              1969
```

<210> SEQ ID NO 4
<211> LENGTH: 2884
<212> TYPE: DNA
<213> ORGANISM: Bombyx mori
<220> FEATURE:

<223> OTHER INFORMATION: hsp90 promoter g2900

<400> SEQUENCE: 4

```
ccatggctca gttcgcttta aatatcgata gtctttaaaa aaaaattatg atgtgaaatc      60
tgaaaaggtt tgcgcactat gcgctcatgc aatttcaact ttaatcaata gccctaaagc     120
agtgctgcca acaaataaaa aaatatttat tgtaagtgag ataactaaat ttgtcagaat     180
tcatcgcttc tttgctattt tttattatgg tttgtgttta attatatttt aaacgtgttg     240
atgaaatagt aagataatta gcattaaatt tacaccactt tcgtgaaggt tttctggcta     300
atcgtttcag tttgtgtggc ataaaactat gggctataac tattgctggt gagactttaa     360
cagcttcata aggacgggtg gattaactca aaaacacagc ttggagggaa agagtttgct     420
aatagccgcc agagtgcctc caaaaggggt ttaatagtac taggacagtt actttacgag     480
tgcatctact ccgtgtcgag aagcttagag ctcagtatca catacaaatc gtcgacgagt     540
tagctgaacc atgcttttat tgctcttggc gttaaaatta gtagtgataa tgagaacgta     600
tcaggtggat cttgcattat ttgaaagatg agactaaaga tctgtaggtt gtgcgagaga     660
atgtcgcgag gcaaaaatag tttcctctac ctgtagataa cgagaacaca aattttatac     720
agggtgtata ggagaagacg aggaacaatt atttttaatga tttctgacat ctaaatgaac     780
aataagattt tacttttgat gaacaaaaca agtaactcac atcttaaact gaacgttact     840
acgttctggt ttgctattgt aattttaatc aatgttttct ccaatctgca ttatgataca     900
ataaagctc attattcgcg tttccttcac tcgcgttttc actattcgca gattaaaatg      960
tgtcccaatt cctatttcg caattaaaga tctcttatt cgcggatcta atcgatacat      1020
agacattgat aaaagaaat ccaatattaa gtattcaact gaatatcctt tataatcgcg     1080
ctataatcac ggtttatcta taagccttg ttcggactag gcgagtattt tagtcgagta     1140
ccgagtaatt tagtagctaa atgtgtccga gcaccaaaag tttagtcgag taggttagta     1200
aataattag taaagccaat ccattttgtt ctattttatc gggcgagtag cgcctcccac     1260
cacgcgtcct agctcactgg ctcactgact aaacaagtcc gaacctgttg attagtcgag     1320
ttcattagtg gcgcttctca aatggaactt tcggacattc ttaaactatc gaagtattct     1380
ttgggatctc ttccaatgct aattctttca gaagacattt atctcttcaa tcgatccatt     1440
ttcgtaccta taacttattt ttcataatca cagaaatttg ctcgtccacc ttttctaaaa     1500
tagccattac gattagctta atcagtttat tcactctatt gcgttgcagt ctgttcatcc     1560
tgcaaaacac cactcacttg tgtactctac tggaccgtaa tgcgaacgat ttctgtgcag     1620
tagcgagtag tttagccact aaattactcg gtactcgact aaaatactcg cctagtccga     1680
acaaggcttt agcgacatat ttacgtaacg tatacacccc gataaagaga tttactgtcc     1740
aaaaaaaacg tcaaaaaatg gaacaaatta tgtgcttttt atttattggt attactaatt     1800
tcgttaagaa tttcatcgga agcagccagc gccgaatgcg gtgaatagta aaactataag     1860
aaggaagcgg ttggaatgat ctgggtaaaa tgttatttct tacgaattac gatgattctt     1920
tgattaaatt tggaaaagtt ttgtggtcaa attatttaac attcatcttg tatcatttat     1980
tgactctaat ttcaactaag ttatttctgt aatgttaaaa tttcgatgct tttctagaat     2040
attcaggaat gttccagata ttcttgtgtg tagatcgtat tgccaccttg tgccaaatag     2100
cggcactaaa ataattcggc agagctatac aacatttggt aatttattt attttgctat     2160
tttccccagt ttttaaatt actgtgtttt taactagcaa ttcatttaa ttggatgcaa      2220
tttacactgc cttaataatt tttttttagt tgtaatttgg tttcttacgt ttatgctgta     2280
```

```
tattttttagt gatctgcaaa atgcgaaaca ctgaacagct taggaaaatt taaaatgtga    2340
gatgtttctt ttacttaaat aaatacttaa aatataacag agaaaaaaca ttttttaacta    2400 gtctggcata ttttagtgaa tctattgatg aaaatgaacg aaatatgtaa ttacctttat    2460
aatttcttga attattttaa ggaaatatat ttttcctaac actttaaact tcaaagcggg    2520
tgatgcaata ataactaaca caaaagaaa cttgcagtgt taagtaaatg attttttctct    2580 tcgttttatg gcctcccaaa atgaaataat tgccaattaa tttgaaatga ttaattattt    2640
ttatttaata ttgtttcggt ttgtattgat ggtaaaatgt tgatgctctc tgacggaaat    2700
agcgtcagaa tcgagaaact tctactgatt catagatgtc gcttgctaga ggaaagtata    2760
aaaacgaatt tacacaccgc gcccggcgtt atttgaacta agagaagtac ggagactaac    2820
gtttgatact ttgcgctttg aaacacgtgt gttaaaaacc ctctagtcat tttgtgtgaa    2880
ttaa                                                                  2884

<210> SEQ ID NO 5
<211> LENGTH: 1555
<212> TYPE: DNA
<213> ORGANISM: Bombyx mori
<220> FEATURE:
<223> OTHER INFORMATION: hsp90 promoter g2900 delta 1-5

<400> SEQUENCE: 5
ggcgcttctc aaatggaact ttcggacatt cttaaactat cgaagtattc tttgggatct      60
cttccaatgc taattctttc agaagacatt tatctcttca atcgatccat tttcgtacct     120
ataacttatt tttcataatc acagaaattt gctcgtccac cttttctaaa atagccatta     180
cgattagctt aatcagttta ttcactctat tgcgttgcag tctgttcatc ctgcaaaaca     240
ccactcactt gtgtactcta ctggaccgta atgcgaacga tttctgtgca gtagcgagta     300
gtttagccac taaattactc ggtactcgac taaaatactc gcctagtccg aacaaggctt     360
tagcgacata tttacgtaac gtatacaccc cgataaagag atttactgtc caaaaaaaac     420
gtcaaaaaat ggaacaaatt atgtgctttt tatttattgg tattactaat ttcgttaaga     480
atttcatcgg aagcagccag cgccgaatgc ggtgaatagt aaaactataa gaaggaagcg     540
gttggaatga tctgggtaaa atgttatttc ttacgaatta cgatgattct ttgattaaat     600
ttggaaaagt tttgtggtca aattatttaa cattcatctt gtcatttta ttgactctaa      660 tttcaactaa gttatttctg taatgttaaa atttcgatgc ttttctagaa tattcaggaa     720
tgttccagat attcttgtgt gtagatcgta ttgccacctt gtgccaaata gcggcactaa     780
aataattcgg cagagctata caacatttgg taattttatt tattttgcta ttttccccag     840
ttttttaaat tactgtgttt ttaactagca attcattta attggatgca atttacactg      900
ccttaataat ttttttttag ttgtaatttg gtttcttacg tttatgctgt atatttttag     960
tgatctgcaa aatgcgaaac actgaacagc ttaggaaaat ttaaaatgtg agatgtttct    1020
tttacttaaa taaatactta aaatataaca gagaaaaaac attttttaact agtctggcat    1080 attttagtga atctattgat gaaaatgaac gaaatatgta attacctta taatttcttg     1140 aattatttta aggaaatata ttttcctaa cactttaaac ttcaaagcgg gtgatgcaat     1200
aataactaac acaaaagaa acttgcagtg ttaagtaaat gattttctc ttcgttttat     1260 ggcctcccaa atgaaataa ttgccaatta atttgaaatg attaattatt tttatttaat     1320
attgtttcgg tttgtattga tggtaaaatg ttgatgctct ctgacggaaa tagcgtcaga    1380
```

```
atcgagaaac ttctactgat tcatagatgt cgcttgctag aggaaagtat aaaaacgaat      1440
ttacacaccg cgcccggcgt tatttgaact aagagaagta cggagactaa cgtttgatac      1500
tttgcgcttt gaaacacgtg tgttaaaaac cctctagtca ttttgtgtga attaa           1555
```

<210> SEQ ID NO 6
<211> LENGTH: 19
<212> TYPE: PRT
<213> ORGANISM: Bombyx mori
<220> FEATURE:
<223> OTHER INFORMATION: signal peptide of serisin 1 from Bombyx mori

<400> SEQUENCE: 6

```
Met Arg Phe Val Leu Cys Cys Thr Leu Ile Ala Leu Ala Ala Leu Ser
1               5                   10                  15

Val Lys Ala
```

<210> SEQ ID NO 7
<211> LENGTH: 57
<212> TYPE: DNA
<213> ORGANISM: Bombyx mori
<220> FEATURE:
<223> OTHER INFORMATION: nucleic acid sequence coding signal peptide of
      serisin 1 from Bombyx mori

<400> SEQUENCE: 7

```
atgcgtttcg ttctgtgctg cactttgatt gcgttggctg cgctcagcgt aaaagct         57
```

<210> SEQ ID NO 8
<211> LENGTH: 18
<212> TYPE: PRT
<213> ORGANISM: Bombyx mori
<220> FEATURE:
<223> OTHER INFORMATION: signal peptide of serisin 2 from Bombyx mori

<400> SEQUENCE: 8

```
Met Lys Ile Pro Tyr Val Leu Leu Phe Leu Val Gly Val Ala Val Val
1               5                   10                  15

Asn Ala
```

<210> SEQ ID NO 9
<211> LENGTH: 54
<212> TYPE: DNA
<213> ORGANISM: Bombyx mori
<220> FEATURE:
<223> OTHER INFORMATION: nucleic acid sequence coding signal peptide of
      serisin 2 from Bombyx mori

<400> SEQUENCE: 9

```
atgaagatcc catacgtctt gctgttcctt gtgggcgtgg ctgtggtcaa cgca            54
```

<210> SEQ ID NO 10
<211> LENGTH: 18
<212> TYPE: PRT
<213> ORGANISM: Bombyx mori
<220> FEATURE:
<223> OTHER INFORMATION: signal peptide of serisin 3 from Bombyx mori

<400> SEQUENCE: 10

```
Met Asn Cys Lys Val Ala Leu Phe Leu Ile Val Ala Ile Val Ala Val
1               5                   10                  15

Gln Ala
```

<210> SEQ ID NO 11

```
<211> LENGTH: 54
<212> TYPE: DNA
<213> ORGANISM: Bombyx mori
<220> FEATURE:
<223> OTHER INFORMATION: nucleic acid sequence coding signal peptide of
      serisin 3 from Bombyx mori

<400> SEQUENCE: 11
atgaattgta aagttgctct attcctgata gtggctattg tagccgtcca ggct            54

<210> SEQ ID NO 12
<211> LENGTH: 24
<212> TYPE: DNA
<213> ORGANISM: Artificial
<220> FEATURE:
<223> OTHER INFORMATION: primer

<400> SEQUENCE: 12
ccatggctca gttcgcttta aata                                             24

<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13
ttaattcaca caaaatgact agaggg                                           26

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
ctagctagcc catggctcag ttcgctt                                          27

<210> SEQ ID NO 15
<211> LENGTH: 28
<212> TYPE: DNA
<213> ORGANISM: Artificial
<220> FEATURE:
<223> OTHER INFORMATION: primer

<400> SEQUENCE: 15
ccgctcgagt taattcacac aaaatgac                                         28

<210> SEQ ID NO 16
<211> LENGTH: 26
<212> TYPE: DNA
<213> ORGANISM: Artificial
<220> FEATURE:
<223> OTHER INFORMATION: primer

<400> SEQUENCE: 16
gctagctcgc gtttccttca ctcgcg                                           26

<210> SEQ ID NO 17
<211> LENGTH: 30
<212> TYPE: DNA
<213> ORGANISM: Artificial
<220> FEATURE:
<223> OTHER INFORMATION: primer
```

-continued

```
<400> SEQUENCE: 17
gctagccgcg gatctaatcg atacatagac                                    30

<210> SEQ ID NO 18
<211> LENGTH: 26
<212> TYPE: DNA
<213> ORGANISM: Artificial
<220> FEATURE:
<223> OTHER INFORMATION: primer

<400> SEQUENCE: 18
gctagcttat cgggcgagta gcgcct                                        26

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
gctagcggcg cttctcaaat ggaactttcg                                    30

<210> SEQ ID NO 20
<211> LENGTH: 33
<212> TYPE: DNA
<213> ORGANISM: Artificial
<220> FEATURE:
<223> OTHER INFORMATION: primer

<400> SEQUENCE: 20
tctagaaaag catcgaaatt ttaacattac aga                                33

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
ctagctagcc cgggctcaag cttgatgcg                                     29

<210> SEQ ID NO 22
<211> LENGTH: 27
<212> TYPE: DNA
<213> ORGANISM: Artificial
<220> FEATURE:
<223> OTHER INFORMATION: primer

<400> SEQUENCE: 22
ccgctcgagt gaattagtct gcaagaa                                       27
```